United States Patent [19]

Denis et al.

[11] Patent Number: 4,946,983

[45] Date of Patent: Aug. 7, 1990

[54] PROCESS FOR THE ACYLATION OF N,N-DIALLYLANILINE OR A MIXTURE OF N,N-DIALLYLANILINE AND N-ALLYLANILINE

[75] Inventors: Jean-Pierre Denis, Doyet; Jean-Roger Desmurs, Communay; Jean-Pierre Lecouve, Caluire, all of France

[73] Assignee: Rhone Poulenc Chimie, Courbevoie, France

[21] Appl. No.: 288,873

[22] Filed: Dec. 23, 1988

[30] Foreign Application Priority Data

Dec. 23, 1987 [FR] France ................................ 87 18012

[51] Int. Cl.$^5$ ............................................. C07C 231/00
[52] U.S. Cl. ...................................... 564/143; 558/418
[58] Field of Search ......................... 564/143; 558/418

[56] References Cited

U.S. PATENT DOCUMENTS

| | | | |
|---|---|---|---|
| 2,538,765 | 1/1951 | Crooks, Jr. et al. | 260/490 |
| 3,962,305 | 6/1976 | Pallos | 260/455 A |
| 4,069,038 | 1/1978 | Teach . | |
| 4,110,105 | 8/1978 | Teach | 71/95 |

FOREIGN PATENT DOCUMENTS 2305434  3/1976  France .

OTHER PUBLICATIONS

Caubere et al., *C.R. Academy of Sciences*, vol. 275, 1972, pp. 1305-1308.

*Primary Examiner*—Richard L. Raymond
*Assistant Examiner*—P. O'Sullivan
*Attorney, Agent, or Firm*—Finnegan, Henderson, Farabow, Garrett, and Dunner

[57] ABSTRACT

A process for the preparation of N-acyl-N-allylaniline. A solution of diallylaniline or a mixture of monoallyl and diallylaniline is placed in contact with a carboxylic acid halide.

16 Claims, No Drawings

PROCESS FOR THE ACYLATION OF N,N-DIALLYLANILINE OR A MIXTURE OF N,N-DIALLYLANILINE AND N-ALLYLANILINE

The present invention relates to a process for the acylation of an N,N-diallylaniline. It relates more particularly to the acylation of N,N-diallyl-meta-trifluoromethylaniline.

According to French Patent No. 2,305,434 it is known that N-dichloroacetyl-N-allyl-meta-trifluoromethylaniline is a compound used as a raw material for the preparation of a highly promising herbicide, 3-N-meta-trifluromethylphenyl-3-chloro-4-chloromethyl-2-pyrrolidone, of the following formula

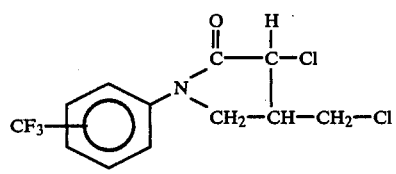

The process for preparing this herbicide consists in cyclizing N-dichloroacetyl-N-allyl-meta-trifluoromethylaniline according to the following reaction

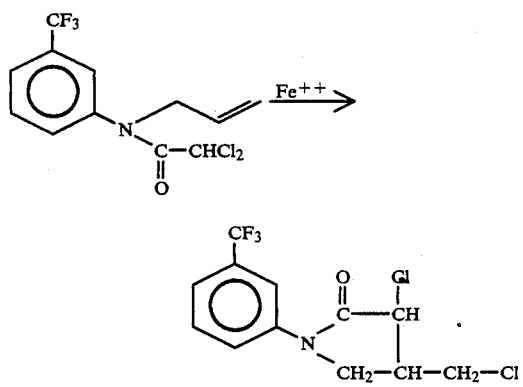

The problem of obtaining this herbicide resides in the preparation of the N-allyl N-acylated derivative. In fact, when a start is made by the allylation of aniline, this leads to a significant quantity of diallyl derivatives which must be removed in order to obtain the monoallylated product which is then acylated. When it is desired to carry out a monoallylation, then the steps of the process disclosed in the abovementioned patent and described below must be followed.

The process disclosed in French Patent No. 2,305,434 for preparing N-allyl-N-dichloroacetylaniline is carried out according to the following 4 steps.

In the first step, a hydrogen atom of the -NH$_2$ group of the aniline is protected with acetic anhydride, in the second step, the allylation is carried out, in the third step, the acyl protective group is removed, and in the fourth step acylation using dichloroacetyl chloride is carried out. The process is illustrated by the following scheme:

first step

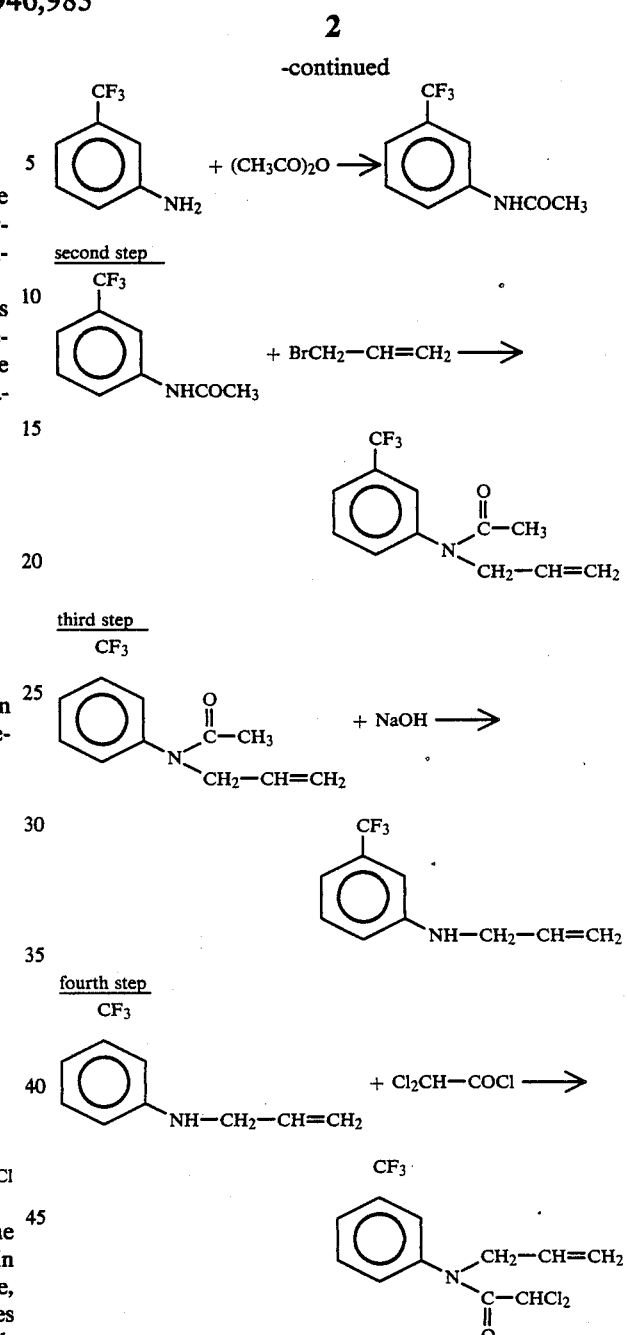

The yield obtained after such a series of steps as disclosed in Example 7 of this French patent is of the order of 36%. This yield is very low and proportionately increases the cost of production of the final herbicide.

The present invention has made it possible to render this process profitable by eliminating the intermediate protections required by the process of French Patent No. 2,305,434. The present invention provides a process whereby it is possible to change directly from an N,N-diallylaniline to an N-allyl-N-acylaniline without isolating the monoallyl intermediate.

An object of the present invention is, therefore, a process for the preparation of N-allyl-N-acylaniline, wherein an N,N-diallylaniline or a mixture of N-mono and N,N-diallylanilines is placed in contact with a carboxylic acid halide, preferably in the presence of a metal catalyst selected from palladium and copper.

The present invention may be applied to a mixture of N-allyl and N,N-diallylanilines, as well as to a pure solution of N,N-diallylaniline.

According to the publication by P. Caubere and J. C. Madelmont, C. R. Academie des sciences, 1972, 275, 1306, it is known to cut tertiary aliphatic amines containing an unsaturated chain on the nitrogen using acid chlorides in the presence of copper in tetrahydrofuran. Cuprous halides alone, and not cupric salts, permit the nitrogen-carbon bond to be cut. Furthermore, the cuprous halides are employed in a stoichiometric quantity relative to the tertiary amine to be cut.

The basicity of the amines of the present invention is very low when compared with that of tertiary aliphatic amines. Therefore, at the time the invention was made it was not obvious that the amines of the present invention could react with the acid chloride to form the intermediate acylium and then decompose to an amide.

Caubere et al. discloses that the reaction is proportionally more difficult the greater the hindrance of the substituents carried by the nitrogen atom and the acyl group. In the present invention, the size of the benzene-derived and dichloromethyl substituents is considerable.

A metal catalyst based on palladium or on copper may be employed within the scope of the present invention. Preferably, these catalysts are in the form of salts, oxides or complexes.

Among the salts, oxides and complexes of the above-mentioned metals, palladium and copper chlorides, palladium acetate and palladium chloride complexed with benzonitrile in an oxidation state of II are suitable. A suitable complex of a metal in a zero oxidation state is dibenzylideneacetonepalladium, and cuprous chloride is a suitable catalyst having a degree of oxidation of I.

Representative N,N-diallylanilines which can be employed within the scope of the present invention include compounds of the formula (I)

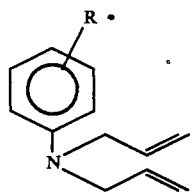

in which R denotes a halogenated group, an alkyl containing 1 to 6 carbon atoms, an alkoxy containing 1 to 6 carbon atoms, an alkylthio containing 1 to 6 carbon atoms, a haloalkyl, a haloalkoxy, a haloalkylthio containing 1 to 6 carbon atoms, a nitro or a cyano group.

The use of N,N-diallyl-meta-trifluoromethylaniline is particularly preferred.

Among the acid halides, chlorides or bromides of carboxylic acids containing 2 to 12 carbon atoms are preferably employed. These acids may be halogenated if desired. Dichloroacetyl chloride is particularly preferred.

The reaction can take place in any solvent such as acetonitrile, benzene and aromatic solvents, alkanes containing at least 6 carbon atoms, water, benzonitrile, dimethylformamide, N-methylpyrrolidone, nitrobenzene, and the acid halide employed in the reaction.

In the process of the present invention it is preferred to employ a quantity of catalyst such that the molar ratio of the metal catalyst to the allylaniline is from about 0.001:1 to 0.1:1, more preferably 0.001:1 to 0.05:1, and most preferably from about 0.001:1 to 0.025:1. The molar ratio of the acid halide to the allylaniline is preferably greater than 1:1.

It is preferred to employ a quantity of solvent such that the concentration of N,N-diallylaniline or a mixture of N-mono and N,N-diallylanilines in the solvent is higher than 50 g/liter.

In accordance with the process of the present invention, it is preferable to conduct the reaction at a temperature from about 20° C. to 120° C. and at atmospheric pressure. However, a higher pressure would not be detrimental to the process of the instant invention.

This invention will be described more completely with the aid of the following examples, which should not, in any event, be construed as limiting the scope of the invention.

The meanings of the legends in the examples which follow are:

$DC$ = the degree of conversion of the starting material
$$DC = \frac{\text{Number of moles of converted material}}{\text{Number of moles of initial material}}$$

$RY$ = the yield based on the initial material
$$RY = \frac{\text{Number of moles of final product}}{\text{Number of moles of initial material}}$$

$CY$ = the yield based on the converted material
$$CY = \frac{\text{Number of moles of final product}}{\text{Number of moles of converted material}}$$

EXAMPLE 1

4 grams of N,N-diallyl-meta-trifluoromethyl-aniline (m-TFMA) (16.6 mmol) were introduced with 5 g of dichloroacetyl chloride (33.9 mmol) into a 100-ml round-bottomed flask, and the mixture was heated to 100° C. for 29 h. The reaction mixture was diluted with 5 ml of ethyl acetate and determined by gas phase chromatography.

| | |
|---|---|
| DC N,N-diallyl-m-TFMA = | 73.38% |
| CY N-dichloroacetyl-N-allyl-m-TFMA = | 80.13% |

EXAMPLE 2

1.0195 grams of N,N-diallyl-m-TFMA (4.34 mmol) were introduced with 1.231 g of dichloroacetyl chloride (8.34 mmol) into a 10-ml round-bottomed flask, with 0.2264 g of dibenzylideneacetonepalladium (Pd(DBA)$_2$) and 2 ml of acetonitrile. The reaction mixture was kept at 20° C. for 48 h, and was diluted with 5 ml of ethyl acetate, after which a gas phase chromatography determination was carried out.

| | |
|---|---|
| DC N,N-diallyl-m-TFMA = | 63.2% |
| CY N-dichloroacetyl-N-allyl-m-TFMA = | 36.6% |

EXAMPLE 3

0.9940 grams of N,N-diallyl-m-TFMA (4.12 mmol) were introduced with 1.2045 g of dichloroacetyl chloride (8.16 mmol), 0.1608 g of PdCl$_2$($\phi$CN)$_2$ (0.42 mmol) and 2 ml of acetonitrile into a 10-ml round-bottomed flask. The reaction mixture was kept at 20° C. for 48 h and a gas phase chromatography determination was then carried out.

| DC N,N-diallyl-m-TFMA = | 39.5% |
|---|---|
| CY N-dichloroacetyl-N-allyl-m-TFMA = | 60.3% |

EXAMPLE 4

2.0171 grams of N,N-diallyl-m-TFMA (8.37 mmol) were introduced with 2.44 g of dichloroacetyl chloride (16.54 mmol), 0.148 g of $PdCl_2$ (0.838 mmol) and 4 ml of acetonitrile into a 10-ml round-bottomed flask. The reaction mixture was heated to 90° C. for 3 h 30 min and a gas phase chromatography determination was then carried out.

| DC N,N-diallyl-m-TFMA = | 100% |
|---|---|
| CY N-dichloroacetyl-N-allyl-m-TFMA ≧ | 95% |

EXAMPLE 5

2.0057 grams of N,N-diallyl-m-TFMA (8.3 mmol) are introduced with 2.4563 g of dichloroacetyl chloride (16.6 mmol), 0.0465 g of $Pd(DBA)_2$ (0.08 mmol) and 4 ml of acetonitrile into a 10-ml round-bottomed flask. The reaction mixture was heated to 80°–85° C. for 7 h 40 min and a gas phase chromatography determination was then carried out.

| DC N,N-diallyl-m-TFMA = | 100% |
|---|---|
| CY N-dichloroacetyl-N-allyl-m-TFMA ≧ | 95% |

EXAMPLES 6 to 10

These examples demonstrate the influence of the solvent on the degree of conversion and yield. The following were charged into a 30-ml reactor 0.48 g of N,N-diallyl-m-trifluoromethylaniline (2 mmol)
0.58 g of dichloroacetyl chloride (4 mmol)
2 ml of solvent
0 2 mmol of $Pd(DBA)_2$.

This mixture was heated to 75° C. for 10 h 40 min. After cooling, 5 ml of N sodium hydroxide were added. The organic products were extracted with 5×5 ml of isopropyl ether. The organic phase was filtered through clarcel and diluted to 25 ml for determination using gas phase chromatography with internal standardization. The degree of conversion for the N,N-diallylaniline (NN Di) and the yield of N-allyl-N-acylaniline (NANA) are reported in Table I.

TABLE I

| Test No. | Solvents | DC NN Di | CY NANA |
|---|---|---|---|
| 6 | $CH_3CN$ | 98.4 | 92.4 |
| 7 | Benzene | 99.9 | 87.2 |
| 8 | Benzonitrile | 96.4 | 100 |
| 9 | Heptane | 99.6 | 85.3 |
| 10 | $H_2O$ | 42.8 | 5.28 |

EXAMPLE 11

This example demonstrates the influence of time of the degree of conversion and yield. The process was carried out as in Example 6 except the reaction time was 5 hours. The results are reported below in Table II.

TABLE II

| Test No. | Solvents | DC NN Di | CY NANA |
|---|---|---|---|
| 11 | Heptane | 100 | 66.8 |

EXAMPLES 12 to 16

These examples demonstrate the influence of the catalyst, the temperature, and time on the degree of conversion and yields. The process was carried out as in Example 6, where 0.2 mmol of catalyst was charged. The results are reported in Table III.

TABLE III

| TEST NO. | CONDITIONS | SOLVENT | CATALYST | DC % NN Di | CY % NANA |
|---|---|---|---|---|---|
| COMPARATIVE 1[1] | 75° C., 7 h | $CH_3CN$ | without | 7.1 | 79.3 |
| 12 | 75° C., 10 h 40 min. | $CH_3CN$ | $Pd(DBA)_2$ | 98.4 | 92.4 |
| 13 | 75° C., 10 h | $CH_3CN$ | $CuCl_2$ | 50.9 | 81.5 |
| 14 | 75° C., 5 h | $CH_3CN$ | $CuCl_2$ | 36 | 53.3 |
| 15 | 70° C., 5 h | $CH_3CN$ | CuCl 10% | 35 | 50.2 |
| COMPARATIVE 2 | 40° C., 7 h | $CH_3CN$ | without | 0 | 0 |
| 16 | 40° C., 7 h | $CH_3CN$ | $Pd(DBA)_2$ | 48.8 | 53 |

[1]Comparative Example 1 falls within the scope of the invention, but is comparative with Example Nos. 12–15 because no catalyst is used.

EXAMPLES 17 to 25

These examples demonstrate the influence of the amount of the catalyst on the acetylation of a mixture of N-allyl and N,N-diallyl.

The process was carried out as in Example 5, the following were initially charged:

0.48 g of N,N-diallyl-m-trifluoromethylaniline (2 mmol)
0.4 g of N-allyl-m-trifluoromethylaniline (2 mmol)
0.58 g of dichloroacetyl chloride (4 mmol )
2 ml of solvent.

TABLE IV

| Test No. | Conditions | Solvent | catalyst % | mol % of catalyst | DC N'allyl % | DC NNDi | CY NANA |
|---|---|---|---|---|---|---|---|
| COMPARATIVE 3 | 75° C.-7h30 | $CH_3CN$ | without | | 100 | 0.5 | 52.1 |
| 17 | 75° C.-7h30 | $CH_3CN$ | $Pd(DBA)_2$ | 2.5 | 100 | 100 | 104 |
| 18 | 75° C.-7h30 | $CH_3CN$ | $Pd(DBA)_2$ | 1 | 100 | 91.5 | 96.9 |
| 19 | 75° C.-7h30 | $CH_3CN$ | $Pd)DBA)_2$ | 0.25 | 100 | 51.4 | 75 |
| 20 | 75° C.-7h30 | $CH_3CN$ | $PdCl_2(phCN)_2$ | 0.25 | 100 | 27.3 | 66.8 |
| 21 | 75° C.-7h30 | $CH_3CN$ | $CuCl_2$ | 10 | 100 | 42 | 70.4 |

TABLE IV-continued

| Test No. | Conditions | Solvent | catalyst % | mol % of catalyst | DC N'allyl % | DC NNDi | CY NANA |
|---|---|---|---|---|---|---|---|
| 22 | 75° C.–7h30 | CH$_3$CN | CuCl$_2$ | 2.5 | 100 | 21.1 | 58.4 |
| 23 | 75° C.–7h30 | CH$_3$CN | CuCl$_2$ | 0.25 | 100 | 12.2 | 57.9 |
| 24 | 75° C.–7h00 | CH$_3$CN | CuCl | 10 | 98.2 | 44 | 62.4 |
| 25 | 75° C.–7h00 | Heptane | Pd(OAc)$_2$ | 10 | 100 | 100 | 76.4 |

What is claimed is:

1. A process for the preparation of N-allyl-N-acylaniline, comprising the step of placing an N,N-diallylaniline or a mixture of N-mono and N,N-diallylanilines in contact with a carboxylic acid halide for a period of time sufficient to produce said N-allyl-N-acylaniline.

2. A process as claimed in claim 1, wherein the N,N-diallylaniline corresponds to the following formula (I)

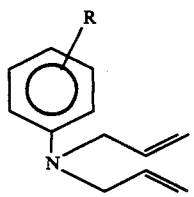

in which R is a halogen group, an alkyl containing 1 to 6 carbon atoms, an alkoxy containing 1 to 6 carbon atoms, an alkylthio containing 1 to 6 carbon atoms, a haloalkyl, a haloalkoxy, a haloalkylthio containing 1 to 6 carbon atoms, a nitro or a cyano group.

3. A process as claimed in claim 2, wherein R is a meta-trifluoromethyl group.

4. A process as claimed in claim 1, wherein the acid halide is selected from bromides and chlorides of carboxylic acids containing 2 to 12 carbon atoms.

5. A process as claimed in claim 4, wherein the acid halide is dichloroacetyl chloride.

6. A process as claimed in claim 1, further comprising a metal catalyst selected from palladium and copper.

7. A process as claimed in claim 6, wherein the metal catalyst is selected from a salt, an oxide and a complex of palladium or copper.

8. A process as claimed in claim 6, wherein the metal catalyst is selected from copper and palladium chlorides, palladium diacetate, dibenzylideneacetonepalladium and PdCl$_2$(DBA)$_2$.

9. A process as claimed in claim 1, wherein the molar ratio of acid halide to allylaniline is greater than 1:1.

10. A process as claimed in claim 1, wherein the molar ratio of the metal catalyst to allylaniline is from about 0.001:1 to 0.1:1.

11. A process as claimed in claim 10, wherein the molar ratio is from about 0.001:1 to 0.05:1.

12. A process as claimed in claim 10, wherein the molar ratio is from about 0.001:1 to 0.025:1.

13. A process as claimed in claim 1, wherein the reaction temperature ranges from about 20° C. to 120° C.

14. A process as claimed in claim 1, further comprising a solvent.

15. A process as claimed in claim 14, wherein the amount of the solvent is such that the concentration of N,N-diallylaniline or a mixture of N-mono and N,N,-diallylaniline in the solvent is approximately greater than or equal to 50 g/liter.

16. A process as claimed in claim 1, wherein the reaction is carried out at atmospheric pressure.

* * * * *